US007573439B2

(12) United States Patent
Lau et al.

(10) Patent No.: US 7,573,439 B2
(45) Date of Patent: Aug. 11, 2009

(54) SYSTEM AND METHOD FOR SIGNIFICANT IMAGE SELECTION USING VISUAL TRACKING

(75) Inventors: Denny Wingchung Lau, Sunnyvale, CA (US); Vijaykalyan Yeluri, Sunnyvale, CA (US); Mark M. Morita, Arlington Heights, IL (US)

(73) Assignee: General Electric Company, Schenectady, NY (US)

( * ) Notice: Subject to any disclaimer, the term of this patent is extended or adjusted under 35 U.S.C. 154(b) by 605 days.

(21) Appl. No.: 11/077,299

(22) Filed: Mar. 10, 2005

(65) Prior Publication Data

US 2006/0109238 A1 May 25, 2006

Related U.S. Application Data

(63) Continuation-in-part of application No. 11/039,152, filed on Jan. 19, 2005, now Pat. No. 7,501,995.

(60) Provisional application No. 60/631,045, filed on Nov. 24, 2004.

(51) Int. Cl.
*G09G 5/00* (2006.01)
(52) U.S. Cl. .............................. 345/7; 345/8
(58) Field of Classification Search ................. 345/7–9, 345/156
See application file for complete search history.

(56) References Cited

U.S. PATENT DOCUMENTS

| 6,106,119 | A | * | 8/2000 | Edwards ...................... 351/209 |
| 6,118,888 | A | * | 9/2000 | Chino et al. ................. 382/118 |
| 6,577,329 | B1 | * | 6/2003 | Flickner et al. ............. 715/774 |
| 6,847,336 | B1 | * | 1/2005 | Lemelson et al. .............. 345/8 |
| 2003/0122839 | A1 | * | 7/2003 | Matraszek et al. .......... 345/581 |
| 2005/0168402 | A1 | * | 8/2005 | Culbertson et al. ............. 345/8 |
| 2006/0007396 | A1 | * | 1/2006 | Clement et al. ............. 345/158 |
| 2006/0256382 | A1 | * | 11/2006 | Matraszek et al. ......... 358/1.18 |

* cited by examiner

*Primary Examiner*—David L Lewis
(74) *Attorney, Agent, or Firm*—Hanley, Flight & Zimmerman, LLC

(57) ABSTRACT

Certain embodiments of the present invention provide a method and system for improved identification of significant images using visual tracking. Certain embodiments of the system include a visual tracking system capable of tracking a user gaze with respect to a display device and a significant image selector for identifying at least one significant image based on user viewing time. The visual tracking system identifies an image at which a user is gazing records a viewing time during which the user is looking at the image. In an embodiment, the visual tracking system records viewing times for one or more users. In an embodiment, meta-data is associated with one or more significant images to identify the images as significant images, for example. The system may further include a database or table storing significant image information.

18 Claims, 3 Drawing Sheets

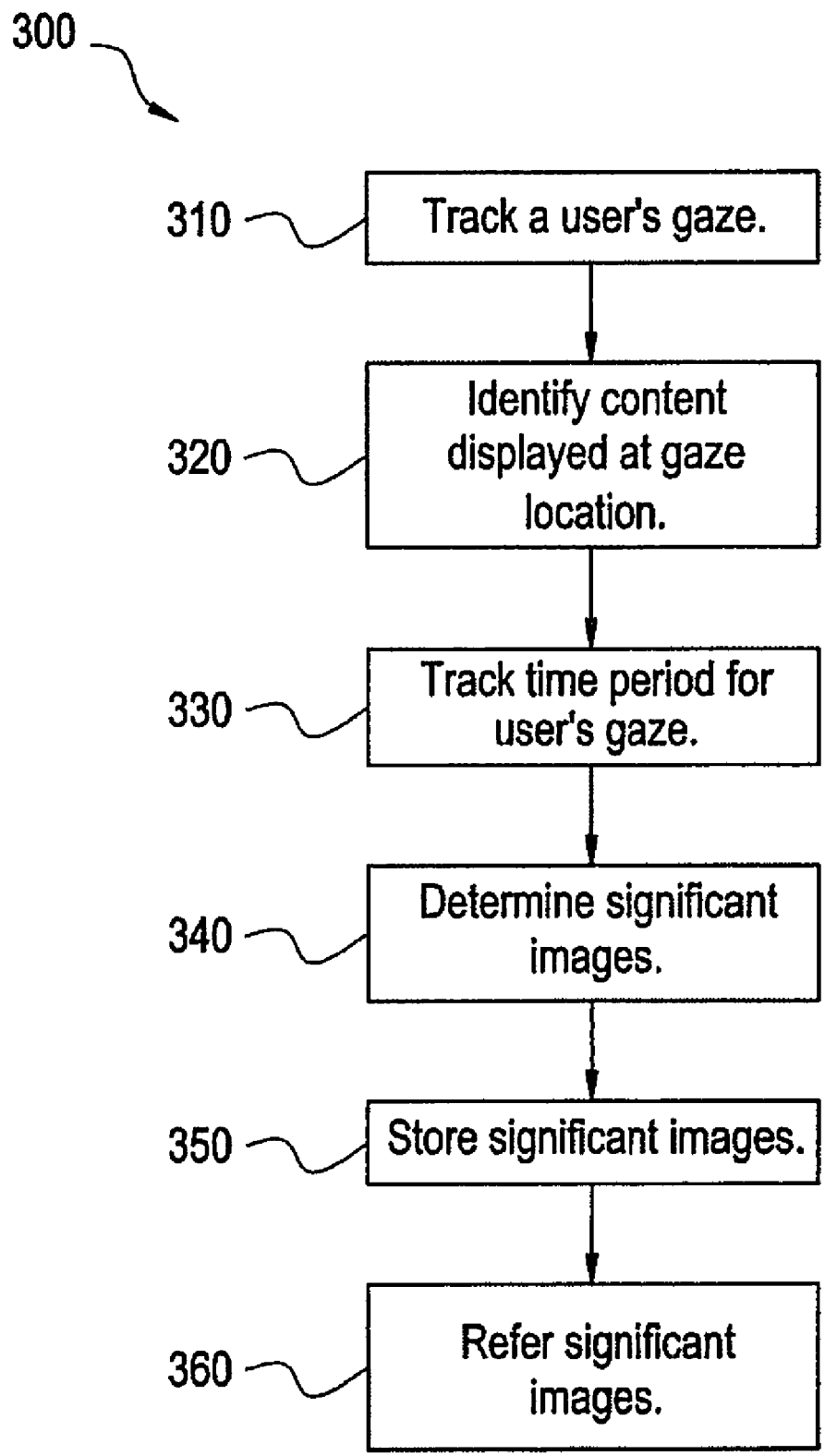

SYSTEM AND METHOD FOR SIGNIFICANT IMAGE SELECTION USING VISUAL TRACKING

RELATED APPLICATIONS

The present application is a continuation-in-part of, and claims priority from, U.S. patent application Ser. No. 11/039,152, filed on Jan. 19, 2005, now U.S. Pat. No. 7,501,995, and entitled "System and Method for Presentation of Enterprise, Clinical, and Decision Support Information Utilizing Eye Tracking Navigation", which claims priority from, U.S. Provisional Application No. 60/631,045, filed on Nov. 24, 2004.

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to display of information in a healthcare environment. In particular, the present invention relates to use of visual tracking technology to improve selection and display of significant images in a healthcare environment.

A clinical or healthcare environment is a crowded, demanding environment that would benefit from organization and improved ease of use of imaging systems, data storage systems, and other equipment used in the healthcare environment. A healthcare environment, such as a hospital or clinic, encompasses a large array of professionals, patients, and equipment. Personnel in a healthcare facility must manage a plurality of patients, systems, and tasks to provide quality service to patients. Healthcare personnel may encounter many difficulties or obstacles in their workflow.

A variety of distractions in a clinical environment may frequently interrupt medical personnel or interfere with their job performance. Furthermore, workspaces, such as a radiology workspace, may become cluttered with a variety of monitors, data input devices, data storage devices, and communication device, for example. Cluttered workspaces may result in efficient workflow and service to clients, which may impact a patient's health and safety or result in liability for a healthcare facility. Data entry and access is also complicated in a typical healthcare facility.

Thus, management of multiple and disparate devices, positioned within an already crowded environment, that are used to perform daily tasks is difficult for medical or healthcare personnel. Additionally, a lack of interoperability between the devices increases delay and inconvenience associated with the use of multiple devices in a healthcare workflow. The use of multiple devices may also involve managing multiple logons within the same environment. A system and method for improving ease of use and interoperability between multiple devices in a healthcare environment would be highly desirable.

In a healthcare environment involving extensive interaction with a plurality of devices, such as keyboards, computer mousing devices, imaging probes, and surgical equipment, repetitive motion disorders often occur. A system and method that eliminate some of the repetitive motion in order to minimize repetitive motion injuries would be highly desirable.

Healthcare environments, such as hospitals or clinics, include information systems, such as hospital information systems (HIS), radiology information systems (RIS), clinical information systems (CIS), and cardiovascular information systems (CVIS), and storage systems, such as picture archiving and communication systems (PACS), library information systems (LIS), and electronic medical records (EMR). Information stored may include patient medical histories, imaging data, test results, diagnosis information, management information, and/or scheduling information, for example. The information may be centrally stored or divided at a plurality of locations. Healthcare practitioners may desire to access patient information or other information at various points in a healthcare workflow. For example, during surgery, medical personnel may access patient information, such as images of a patient's anatomy, that are stored in a medical information system. Alternatively, medical personnel may enter new information, such as history, diagnostic, or treatment information, into a medical information system during an ongoing medical procedure.

In current information systems, such as PACS, HIS, RIS, CIS, CVIS, LIS, and/or EMR, information is entered or retrieved using a local computer terminal with a keyboard and/or mouse. During a medical procedure or at other times in a medical workflow, physical use of a keyboard, mouse or similar device may be impractical (e.g., in a different room) and/or unsanitary (i.e., a violation of the integrity of an individual's sterile field). Re-sterilizing after using a local computer terminal is often impractical for medical personnel in an operating room, for example, and may discourage medical personnel from accessing medical information systems. Thus, a system and method providing access to a medical information system without physical contact would be highly desirable to improve workflow and maintain a sterile field.

Imaging systems are complicated to configure and to operate. Often, healthcare personnel may be trying to obtain an image of a patient, reference or update patient records or diagnosis, and ordering additional tests or consultation. Thus, there is a need for a system and method that facilitate operation and interoperability of an imaging system and related devices by an operator.

In many situations, an operator of an imaging system may experience difficulty when scanning a patient or other object using an imaging system console. For example, using an imaging system, such as an ultrasound imaging system, for upper and lower extremity exams, compression exams, carotid exams, neo-natal head exams, and portable exams may be difficult with a typical system control console. An operator may not be able to physically reach both the console and a location to be scanned. Additionally, an operator may not be able to adjust a patient being scanned and operate the system at the console simultaneously. An operator may be unable to reach a telephone or a computer terminal to access information or order tests or consultation. Providing an additional operator or assistant to assist with examination may increase cost of the examination and may produce errors or unusable data due to miscommunication between the operator and the assistant. Thus, a method and system that facilitate operation of an imaging system and related services by an individual operator would be highly desirable.

A reading, such as a radiology or cardiology procedure reading, is a process of a healthcare practitioner, such as a radiologist or a cardiologist, viewing digital images of a patient. The practitioner performs a diagnosis based on a content of the diagnostic images and reports on results electronically (e.g., using dictation or otherwise) or on paper. The practitioner, such as a radiologist or cardiologist, typically uses other tools to perform diagnosis. Some examples of other tools are prior and related prior (historical) exams and their results, laboratory exams (such as blood work), allergies, pathology results, medication, alerts, document images, and other tools. For example, a radiologist or cardiologist typically looks into other systems such as laboratory information, electronic medical records, and healthcare information when reading examination results.

Hospitals and other healthcare environments currently have many disparate enterprise information systems that are not integrated, networked or in communication with each other. Currently, a practitioner must log on to different systems and search for a patient to retrieve information from the systems on that patient. During a diagnostic interpretation process, when practitioners use a variety of clinical information to make a diagnosis, for example, practitioners must physically locate workstations containing specific information that they are seeking. Practitioners must log-in, navigate to a particular patient, and then "drill down" or locate a specific kernel of information. Practitioners must currently undertake this manual process for each bit of information they are seeking.

For example, a radiologist identifies a mass in a patient's kidney. Before diagnosing, the radiologist is interested in particular lab results, such as PT (blood clotting), Creatinine, Gleason Score, etc. Currently, a radiologist must access different systems to obtain all of the lab results. Thus, the radiologist may be presented with a large amount of information to review. The radiologist then uses a workstation to parse the lab results and identify the specific desired information. The radiologist must then remember the values and interpretation of the values and enter the values and interpretation into his or report. Such a process may be time consuming. Thus, a system and method providing increased integration between systems and information would be highly desirable.

Depending upon vendors and systems used by a practitioner, practitioners, such as radiologists or cardiologists, have only a few options to reference the tools available. First, a request for information from the available tools may be made in paper form. Second, a practitioner may use different applications, such as a RIS, PACS, EMR, HIS, CIS, CVIS, and LIS, to search for patients and examine the information electronically.

In the first case, the practitioner shifts his or her focus away from a reading workstation to search and browse through the paper, which in most cases includes many pieces of paper per patient. This slows down the practitioner and introduces a potential for errors due to the sheer volume of paper. Thus, a system and method that reduce the amount of paper being viewed and arranged by a practitioner would be highly desirable.

In the second case, electronic information systems often do not communicate well across different systems. Therefore, the practitioner must log on to each system separately and search for the patients and exams on each system. Such a tedious task results in significant delays and potential errors. Thus, a system and method that improve communication and interaction between multiple electronic information systems would be highly desirable.

Additionally, even if systems are integrated using mechanisms such as Clinical Context Object Workgroup (CCOW) to provide a practitioner with a uniform patient context in several systems, the practitioner is still provided with too much information to browse through. Too much information from different applications is provided at the same time and slows down the reading and analysis process. There is a need to filter out application components that a user will not need in a routine workflow. Thus, a system and method which manage information provided by multiple systems would be highly desirable.

Additionally, radiologists, cardiologist, or other healthcare practitioners may repeatedly view similar types of exams during a reading or other review. Currently, PACS and other medical information systems lack tools to extract interpretation behavior of healthcare practitioners to customize workflow. That is, workflow, such as a radiology or cardiology workflow, is designed by PACS or other medical information system developers and is not customized for particular practitioners or types of practitioners. The PACS or other system does not adapt to interpretation patterns of the user, such as a radiologist or cardiologist. Thus, a practitioner's efficiency at using a PACS workstation or other system workstation may no improve over time. A system and method that improves customization of workflow for a practitioner would be highly desirable.

One type of interpretation behavior that may be recorded is a length of time that a practitioner, such as a radiologist or cardiologist, views each image in an exam, for example. A practitioner, such as a radiologist or cardiologist, may focus primarily on certain images ("significant images") to perform an analysis. Identification of significant images reduces a number of images a referral physician or other practitioner examines for diagnosis and/or treatment of a patient. Currently, significant images are manually identified by the practitioner from the images viewed in an exam. Thus, there is a need for a system and method to improve selection and display of significant images in a healthcare environment.

Currently, a healthcare environment such as an operating room (OR) includes multiple displays (CRT, LCD, etc.) connected to multiple, disparate information and/or imaging systems. The displays may be hanging on boom mounted arms from walls, ceilings, tables, and/or floors, for example. In some healthcare settings, such as an OR, ten or more displays may clutter the room and cause great difficulty for practitioners trying to locate key information without scanning each display.

When practitioners wish to access information from the disparate systems, the practitioners must currently turn their heads to look up at the multiple displays and determine which display holds the desired information. Head movement, particularly during a medical procedure, is neither ergonomically correct nor comfortable for the practitioner. Additionally, such head movement may be very repetitive throughout an examination or procedure. Thus, a system and method that reduce head movement and improves ergonomics in a healthcare environment would be highly desirable.

In addition, multiple displays results in an overabundance of information presented simultaneously to a healthcare practitioner. Thus, too much information on too many displays creates difficulty for a practitioner attempting to locate relevant information. Therefore, there is a need for a system and method to improve identification of key information and reduce display clutter in a healthcare environment.

Further difficulties may arise from having too many displays in a healthcare environment, such as an OR. For example, multiple displays are not cost effective from an information technology perspective. Purchasing multiple displays for one or more rooms represents a significant expense for a healthcare provider. Additionally, for example, multiple displays and/or multiple systems generate additional heat in a healthcare environment. Excess heat contributes to higher electric bills and may pose a health hazard to patients, practitioners, and equipment in a healthcare environment. Therefore, a system that reduces multiple displays in a healthcare environment would be highly desirable.

Thus, there is a need for a system and method to improve selection and display of significant images in a healthcare environment.

BRIEF SUMMARY OF THE INVENTION

Certain embodiments of the present invention provide a method and system for improved identification of significant images using visual tracking. Certain embodiments of the system include a visual tracking system capable of tracking a user gaze with respect to a display device and a significant image selector for identifying at least one significant image based on user viewing time. The visual tracking system identifies an image at which a user is gazing records a viewing time during which the user is looking at the image. In an embodiment, the visual tracking system records viewing times for one or more users.

The system may also include a display device capable of displaying images and data. Additionally, the system may include a data store for storing one or more significant images. In an embodiment, meta-data is associated with one or more significant images to identify the images as significant images, for example. The system may further include a database or table storing significant image information. In an embodiment, the system may include an arbitration module for arbitrating among a plurality of users. The system may also include an authentication module for authenticating a user.

Certain embodiments of a method for improved significant image identification include tracking a location of a user gaze in relation to a reference position, identifying an image at the location, recording a viewing time by the user with respect to the image, and designating the image as a significant image based on the viewing time. The method may further include storing the image as a significant image. Additionally, the method may include referring the significant image, such as referring the significant image to a physician. In an embodiment, an image may be designated as a significant image based on a comparison of the viewing time with at least one of a threshold and a second viewing time for a second image, for example.

In an embodiment, the method includes recording viewing times for a plurality of images. One or more significant images may be designated based on viewing times greater than a threshold, for example. One or more significant images may be designated based on a predefined number of longest viewing times, for example.

Certain embodiments provide a computer-readable storage medium including a set of instructions for a computer. The set of instructions includes a gaze detection routine for determining an image that a user is viewing, a timer routine for tracking a viewing time during which the user views the image, and a significant image selection routine for selecting at least one significant image based on the viewing time. In an embodiment, the significant image selection routine selects at least one significant image based on longest viewing time, most frequent viewing time, and/or most recent viewing time. In an embodiment, the significant image selection routine selects at least one significant image based on viewing times greater than a threshold and/or a predefined number of longest viewing times. In an embodiment, the significant image selection routine modifies meta-data associated with at least one significant image to identify the at least one significant image. The set of instructions may also include a referral routine for referring at least one significant image.

BRIEF DESCRIPTION OF SEVERAL VIEWS OF THE DRAWINGS

FIG. 3 shows a flow diagram for a method for significant image selection using visual tracking in accordance with an embodiment of the present invention.

Figure 1:
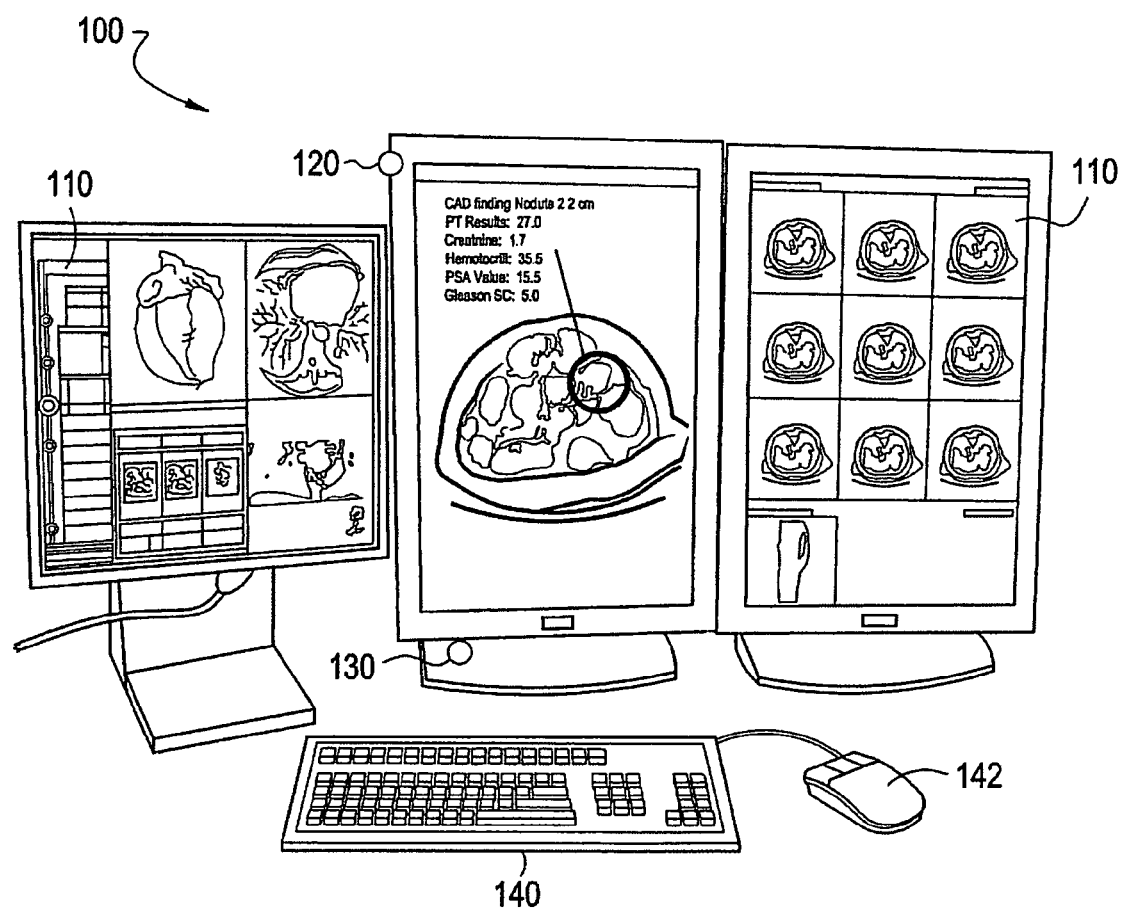
FIG. 1 illustrates an improved display system for selecting and displaying information in accordance with an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

FIG. 1 illustrates an improved display system 100 for selecting and displaying information in accordance with an embodiment of the present invention. The system 100 includes a display 110, a tracking device 120, microphone 130, and manual input devices 140, 142. The components of the system 100 may communicate via wired, wireless and/or infrared communication, for example. The components of the system 100 may be implemented separately and/or integrated in various forms, for example.

As shown in FIG. 1, one or more simple display devices 110 may be used to display information to a user. The display 110 may be used with a camera and/or a portable eyewear and eye tracking system, such as a gaze or visual tracking system including the tracking device 120, to display information for one or more users. By tracking where a user is focusing or fixating his or her visual attention, an accurate measure of user intent may be inferred. Eye or gaze tracking may be faster and more efficient than a mechanical pointing or selecting device, such as a keyboard 140 or mouse 142.

Additionally, voice commands and/or gesture control using cameras, such as fire-wire web cams, may allow interaction with imaging and information systems without disrupting a sterile field. The tracking device 120 may be used in conjunction with gesture control, for example. The microphone 130 may be used in conjunction with voice or subvocal command and control, for example.

The tracking device 120 may be a camera, for example. The tracking device 120 may work instead of and/or in conjunction with a headset or eyewear worn by a user, for example (not shown). The tracking device 120 may be attached to the display device 110, such as on a side or top of the display device 110.

A visual or gaze tracking system may be based on a camera system (e.g., visible light or infrared), for example, and may be active or passive. Alternatively or in addition, a user's gaze may be tracked based on movement of the user's head via a camera or position sensor, for example. Multiple cameras may be used to track a location of a user's gaze. Additionally, multiple cameras may be used to drive a cursor or other indicator on a display, such as the display device 110. The gaze tracking system may include head gear, such as goggles or other ocular device, for a user to wear and/or may use a display-mounted camera or sensor, for example. In an embodiment, the gaze tracking system is calibrated for a user.

By tracking a user's gaze, a system may initiate communication, selection, and/or function at a remote system, for example.

Figure 2:
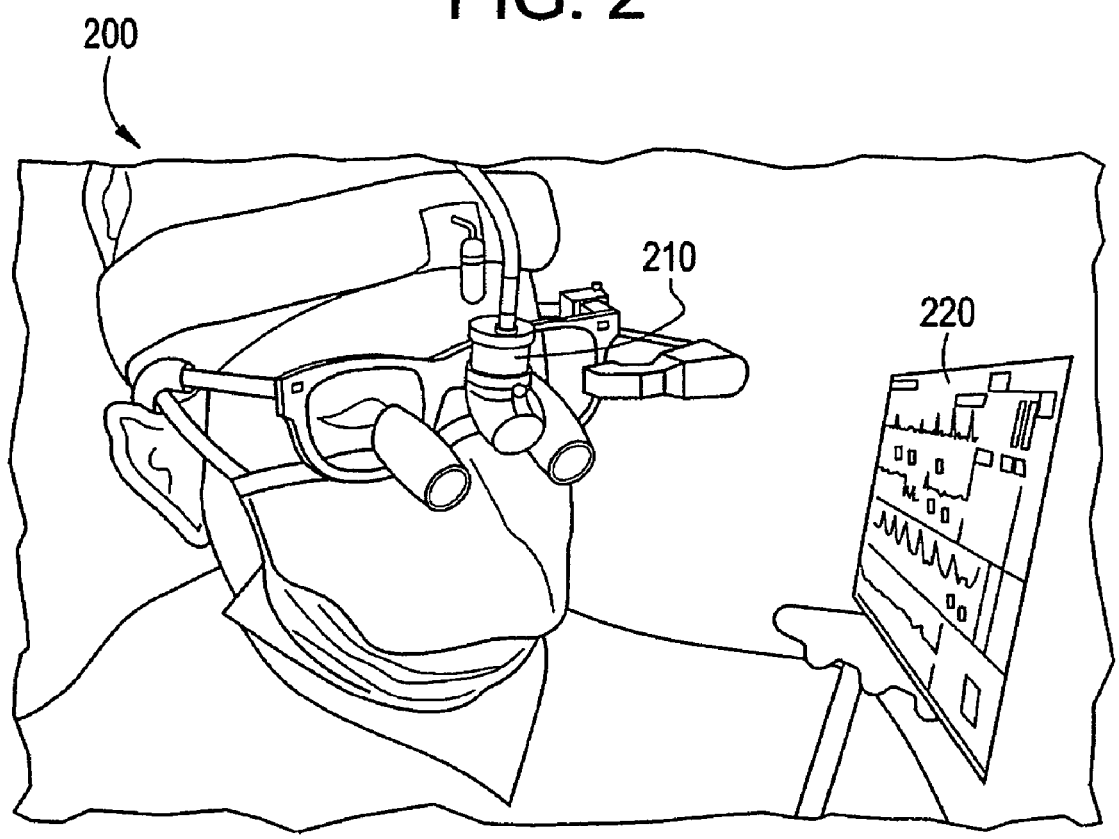
FIG. 2 depicts a portable eyewear viewing system used in accordance with an embodiment of the present invention.

FIG. 2 depicts a portable eyewear viewing system 200 used in accordance with an embodiment of the present invention. The system 200 includes an eyewear headset 210, a personal eyewear display 220, and a gaze tracking processor 230. The processor 230 may be integrated into the eyewear 210 and/or separate from the eyewear 210. The personal eyewear display 220 is projected in a user's field of view by the eyewear 210.

A healthcare practitioner may use eyewear 210, such as goggles, to capture the practitioner's gaze and perform interface navigation. A user's gaze may be tracked via infrared or other light source, for example. Light may be reflected off of the user's pupil(s) and detected. Light may also be reflected off of the front and rear surfaces of the cornea(s) and lenses of the user's eye(s) and detected or recorded. Repeated measurements track a change in the user's gaze. Alternatively or in addition, a user's gaze may be tracked based on movement of the user's head via a camera or position sensor, for example. A position of the user's gaze and/or head in a reference coordinate system and/or with respect to a reference point, such as a location on a display, may be determined. In an embodiment, a plurality of measurements may be obtained to determine a user's line of sight and/or head angle, for example.

In an embodiment, goggles or other eyewear may also project images into a user's oculars or provide a miniature screen attached to the eyewear 210 and positioned in the user's field of vision to form a virtual personal display 220. Thus, eyewear 210 may be used to eliminate some displays in the healthcare environment. Additionally, eyewear 210 may allow specific information to be targeted for display for specific users in the healthcare environment. For example, a nurse, an anesthesiologist, and a surgeon receive different information displayed on their personal eyewear display 220. For example, a surgeon may view image-guided surgery and PACS data while an anesthesiologist views EKG and dosage data. In an embodiment, each user may view customized information without turning to look at a display to select the information.

In an embodiment, the eyewear 210 is a portable eyewear viewer that displays key dynamic patient information such as hemodynamic data, cardiology waveforms, vital signs, etc. Eyewear 210 allows a user to view information without turning his or her head to view an LCD or CRT monitor. Although the eyewear headset 210 allows users to view data while working "heads down" on a patient, resolution may be limited for image review and/or fine text review, for example. When a user wishes to view detailed information or a finer degree of granularity, the user may look at a larger display device in the healthcare environment.

An eye or gaze tracking capability of the headset 210 and/or processor 230 may be used to control a display device, such as the display device 110. For example, the processor 230 detects when a user is looking at a certain button, option or feature on a display and selects or activates the button, option or feature for the user. Activation of an option/feature may also be based on an amount of time a user is looking/has looked at a certain area. The eyewear system 200 may also be used in conjunction with voice commands and/or gestures to control the display device 110 and/or other systems or features, for example.

In an embodiment, a user looks at the display device 110. The gaze tracking processor 230 recognizes that the user wants to see certain information and displays context-sensitive information for the patient on the display device 110, for example. Information on gaze and/or head position may be relayed from the processor 230 to determine information on the display device 110. Additionally, user preference information, information from the display device 110, and/or other input may be transmitted to configure the contents and/or other parameters of the display device 110.

In an embodiment, information displayed on the display device 110 may be determined based on rules and/or perspectives, for example. For example, rules determine that a doctor's gaze takes precedence over a nurse's gaze. Then, when the doctor turns away from the display device 110, the nurse gains control of the display device 110. Alternatively, control of the display device 110 may be shared by multiple users and common information displayed on display device 110 so that multiple users may be accommodated at approximately the same time.

The processor 230 and/or other processor or system related to the display device 110 may have an ability to arbitrate conflicts and priority among a plurality of users seeking access determine which user(s) should take control of the display device 110. For example, rules-based display control and/or hanging protocols may govern which user has control and priority and/or which users may share control and display area. Rules and other protocols may also govern when control over the display device 110 is relinquished and/or preempted.

In an embodiment, video switchboxes and/or voice commands may be used with image-guided surgery to switch displays so that only image-guided surgery information is viewed. In an embodiment, voice control and/or gestures may be used in conjunction with eye tracking to control the display device 110 and/or a system cursor.

In an embodiment, a user, such as a radiologist, may review images via the display device 110. The user may identify one or more of the images as significant images. In an embodiment, access to significant images may be streamlined or shortcut. For example, a user may access one or more significant images with a single click of a mouse button or other simple selection to reduce a user's effort in locating significant images when reviewing an exam or collection of images. A medical information system, such as a PACS system, may store significant image information to enable simplified retrieval of significant images by a user.

A visual tracking system, such as the tracking system 120 and/or the viewing system 200, may be integrated into an information system, such as a PACS workstation, and/or work in conjunction with an information system to track an amount of time a user, such as a radiologist, spends viewing each image in an exam or collection, for example. The visual tracking system may be used to track a location at the display device 110 at which the user is looking. Based on location and duration information, the information system, such as a PACS, may present images to the user, such as a radiologist, in a more efficient manner.

In an embodiment, one or more significant images for a user may be selected automatically based on the length of time an image has been viewed by the user. For example, the images viewed for longer than a certain time period are automatically selected as significant images. The time period may be selected by a user, administrator, system parameter, and/or experimental data, for example. Alternatively, a system may be configured to store a certain number (n) of significant images for a user. The n images viewed for the longest period of time by the user are then denoted as significant images, for example. Viewing times may be stored as meta-data, for example, associated with each image. In another embodiment, most recently viewed images may be stored for a user.

For example, the n most recently viewed images and/or images viewed within a certain time period may be stored for a user or group of users.

For example, for a CT abdominal pelvis exam, images in the top five percent of viewing durations are automatically selected as significant images. For example, a PACS server stores viewing or dwell times for a radiologist for an exam including 6 images based on gaze or other visual tracking. The viewing times are 1390 ms for image 1, 3908 ms for image 2, 1970 ms for image 3, 9077 ms for image 4, 9660 ms for image 5, and 3433 ms for image 6. Images 4 and 5 are selected as significant images based on the viewing times.

The significant images may be flagged using meta-data stored in or with the images or denoted in a table or database, for example. In an embodiment, a user may be alerted to the detection and storage of significant images. The user may review the selected significant images and modify significant image designation if desired. Significant image identification may occur automatically and/or may be triggered by a user via software or other electronic trigger, for example. In an embodiment, gaze-based significant image selection may be augmented by and/or work in conjunction with voice command and mousing device input, for example. In an embodiment, significant images and/or a report, such as a radiology report, may be transmitted automatically or by a user to another practitioner, such as a specialist or referral physician, for review.

A visual tracking system, such as the tracking system 120 and/or the viewing system 200, may be used to track user dwell or gaze time for images on display device 110. The visual tracking system may be a separate system or may be integrated with a PACS or other medical system, for example. In an embodiment, user dwell time is measured when the user is looking at an image. The visual tracking system does not track dwell time when the user is looking at text, buttons, or other peripheral content, for example. The tracking system tracks a user's gaze in relation to the display device 110. The user's gaze location on the display device 110 may be mapped to content displayed at display device 110. The system may determine at which content the user is looking. The visual tracking system or other processor or software may compare image dwell times to determine significant images based on criteria, such as a minimum time threshold, a minimum and/or maximum number of images, etc.

In an embodiment, rather than manually positioning a cursor over an image or part of an image using a mousing device or keyboard, for example, a visual or gaze tracking system may be used to indicate a location on the display device 110. That is, a visual tracking system, such as one using the tracking device 120, may determine a focus of the user's gaze. The tracking system may also determine a "dwell time" or length of time that the user focuses on a location. If a user focuses on a location for at least a certain period of time, the tracking system may position a cursor at that location on the display device 110, for example. The tracking system may also activate a function with respect to the location and/or retrieve information based on the location, for example. In an embodiment, gazing at a certain location for a certain length of time generates a "roll-over" or overlay of supporting information at the display device 110. For example, if a radiologist is gazing at an image of a kidney, a roll-over is displayed to provide supporting information to allow the radiologist to better understand the case.

In an embodiment, a display area of the display device 110 is mapped with respect to a coordinate system, such as an x-y coordinate system. Areas in an image are mapped to x,y coordinates or other location information, for example. Mapping allows the system to determine what area of an image corresponds to the location of a user's gaze or cursor, for example. Then, the system may store and/or retrieve information related to the area in the image and/or on the display 110. The display device 110 and tracking system may be calibrated to map specific locations in specific types of exam studies, such as modality, body part, etc.

In an embodiment, the visual tracking system and display device may work together with a rules-based context manager to filter and display information. One example of a rules-based context manager is described in a U.S. patent application filed on Oct. 1, 2004, entitled "System and Method for Rules-Based Context Management in Radiology and Cardiology Diagnostic Reading", with inventors Prakash Mahesh, Mark M. Morita, and Thomas A. Gentles, which is herein incorporated by reference in its entirety.

In an embodiment, the visual tracking system and display device may work with a perspectives management system for handling multiple applications and workflow. The perspectives management system allows various perspectives to be defined which save workflow steps and other information for a particular user. Perspectives allow a personalized information display to present relevant information germane to a patient's current condition, for example. One example of a perspectives management system is described in a U.S. patent application filed on Oct. 1, 2004, entitled "System and Method for Handling Multiple Radiology Applications and Workflows", with inventors Prakash Mahesh and Mark Ricard, which is herein incorporated by reference in its entirety. For example, in a surgical OR there may be numerous healthcare practitioners at an OR table who use specific perspectives or views of relevant patient information. With a single, large format display (e.g., an LCD, plasma display, 46" display, etc.), each user has the ability to view their personal perspectives on the display in large and/or small format. The display may be shared among the users.

In an embodiment, the visual tracking system may work in conjunction with one or more systems, such as diagnostic review workstations. Diagnostic review workstations may be used to access enterprise clinical information, for example. For example, a radiologist may access clinical information relevant to a current exam in a "just in time" fashion. One example of a diagnostic review or support system is described in a U.S. patent application filed on Jan. 19, 2005, entitled "System and Method for Presentation of Enterprise, Clinical, and Decision Support Information Utilizing Eye Tracking Technology", with inventors Mark M. Morita, Prakash Mahesh, and Thomas A. Gentles, which is herein incorporated by reference in its entirety. For example, the visual tracking system may be used in conjunction with a decision support or information retrieval system to provide additional resources and capabilities for a user.

FIG. 3 shows a flow diagram for a method 300 for significant image selection using visual tracking in accordance with an embodiment of the present invention. First, at step 310, a user's gaze is tracked. For example, the user's gaze may be tracked via eyewear and/or camera(s). The user's gaze may be tracked in relation to a display device to determine an area on the display device at which the user is looking.

Then, at step 320, content displayed at the location at which the user is gazing is identified. For example, if the user is looking at an image of a chest scan on a display screen, the chest scan image is identified. Next, at step 330, a time period during which the user focuses on an image is tracked. The time period, such as a number of seconds, may be stored as meta-data integrated with or associated with the image, for example. Alternatively or in addition, the time period may be stored in a file, table or database associated with the image.

At step 340, significant images are determined. For example, dwell time periods are compared to determine the most viewed and/or longest viewed images. The images with the largest dwell times may be designated as significant images, for example.

Then, at step 350, significant images may be stored. For example, significant images may be stored in a database or other data storage or memory. Alternatively or in addition, meta-data or other data associated with the significant images may be modified to designate the images as significant images, for example.

Next, at step 360, significant images may be referred. For example, a radiologist may refer the significant images to a specialist for review. In an embodiment, a practitioner may automate a referral once significant images are identified.

In an embodiment, a user may modify visual tracking system parameters and/or significant image designations. In an embodiment, the visual tracking system may authenticate a user prior to tracking viewing time and identifying significant images. In an embodiment, the visual tracking system may arbitrate between a plurality of users viewing the display device. Viewing times used to identify significant images may be collected from a single user or from a plurality or group of users, for example.

Thus, certain embodiments help facilitate efficient identification of and access to images important or significant to a healthcare practitioner's diagnosis and/or treatment of a patient. Certain embodiments help increase radiologist and other practitioner productivity by extracting information regarding image interpretation behavior. Certain embodiments present extracted information to the practitioner to allow the practitioner to review an exam or collection of images more efficiently during a subsequent viewing. Additionally, significant images are automatically selected rather than manually indicated. Certain embodiments correlate an amount of time spent viewing an image with designation of the image as a significant image. Certain embodiments store viewing time as meta-data for an image. Certain embodiments provide a visual tracking system used for medical image review.

Furthermore, repetitive head and neck movements may be reduced by minimizing use of traditional manual input devices resulting in a reduction in ergonomic difficulties and stress disorders. Wireless and minimally invasive product design allows easy-to-use, comfortable interaction. Thus, certain embodiments allow users to naturally interact with image(s), interface(s) and/or other information on which they are focused.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A system for visual identification of significant images, said system comprising:
    a visual tracking system capable of tracking a user gaze with respect to at least one medical display device, wherein said visual tracking system identifies an image at which a user is gazing and wherein said visual tracking system records a user viewing time during which said user is looking at said image;
    a significant image selector for identifying at least one significant image based on said user viewing time;
    a medical image database for storing medical images; and
    an arbitration module for arbitrating among a plurality of users
    wherein significant images are designated as significant in said medical image database.

2. The system of claim 1, wherein said visual tracking system records viewing times for one or more users using the medical imaging system at the same time.

3. The system of claim 1, further comprising a display device capable of displaying images and data.

4. The system of claim 1, further comprising meta-data associated with said at least one significant image, wherein said meta-data identifies said at least one significant image as a significant image.

5. The system of claim 1, further comprising a database or table including significant image information.

6. The system of claim 1, further comprising an authentication module for authenticating a user.

7. A method for improved significant image identification using a computer, said method:
    arbitrating among a plurality of viewers to determine at least one user for gaze tracking;
    tracking at least one location of a user gaze for said at least one user in relation to a reference position using a tracking system;
    identifying at least one image at said at least one location;
    recording a viewing time by said at least one user with respect to said image;
    designating said at least one image as a significant image based on said viewing time; and
    storing images in a medical image database such that significant images are designated as significant in said medical image database.

8. The method of claim 7, wherein said recording step further comprises recording viewing times for a plurality of images.

9. The method of claim 8, wherein said designating step further comprises designating at least one significant image based on viewing times greater than a threshold.

10. The method of claim 8, wherein said designating step further comprises designating at least one significant image based on a predefined number of longest viewing times.

11. The method of claim 7, wherein said designating step further comprises designating said image as a significant image based on a comparison of said viewing time with at least one of a threshold and a second viewing time for a second image.

12. The method of claim 7, further comprising referring said significant image.

13. A computer-readable storage medium including a set of instructions for a computer, the set of instructions comprising:
    an arbitration routine for arbitrating conflicts among a plurality of users;
    a gaze detection routine for determining an image that a user is viewing;
    a timer routine for tracking a viewing time during which said user views said image;
    a significant image selection routine for selecting at least one significant image based on said viewing time; and
    a storage routine for storing said at least one significant image in a database such that said significant images are designated as significant in said database.

14. The set of instructions of claim 13, wherein said significant image selection routine selects at least one significant image based on at least one of longest viewing time, most frequent viewing time, and most recent viewing time.

15. The set of instructions of claim 13, wherein said significant image selection routine selects at least one significant image based on at least one of viewing times greater than a threshold and a predefined number of longest viewing times.

16. The set of instructions of claim 13, wherein said significant image selection routine modifies meta-data associated with said at least one significant image to identify said at least one significant image.

17. The set of instructions of claim 13, further comprising a referral routine for referring said at least one significant image.

18. The method of claim 7, wherein said at least one user is a plurality of users, and said at least one location is a plurality of locations.

* * * * *

UNITED STATES PATENT AND TRADEMARK OFFICE
CERTIFICATE OF CORRECTION

PATENT NO.       : 7,573,439 B2                                         Page 1 of 1
APPLICATION NO.  : 11/077299
DATED            : August 11, 2009
INVENTOR(S)      : Lau et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 788 days.

Signed and Sealed this

Seventh Day of September, 2010

David J. Kappos
*Director of the United States Patent and Trademark Office*